(12) United States Patent
Mentkow et al.

(10) Patent No.: US 8,609,129 B2
(45) Date of Patent: Dec. 17, 2013

(54) HEMOSTATIC AGENT COMPOSITION, DELIVERY SYSTEM AND METHOD

(76) Inventors: Jack Mentkow, Wellington, FL (US); Lisa Mentkow, Wellington, FL (US)

( * ) Notice: Subject to any disclaimer, the term of this patent is extended or adjusted under 35 U.S.C. 154(b) by 744 days.

(21) Appl. No.: 12/719,418

(22) Filed: Mar. 8, 2010

(65) Prior Publication Data

US 2010/0158989 A1 Jun. 24, 2010

Related U.S. Application Data

(63) Continuation-in-part of application No. 12/191,323, filed on Aug. 14, 2008, now Pat. No. 8,409,629, and a continuation-in-part of application No. 11/453,524, filed on Jun. 15, 2006.

(60) Provisional application No. 60/964,955, filed on Aug. 16, 2007, provisional application No. 60/757,459, filed on Jan. 9, 2006, provisional application No. 61/158,169, filed on Mar. 6, 2009, provisional application No. 61/158,188, filed on Mar. 6, 2009, provisional application No. 61/158,193, filed on Mar. 6, 2009.

(51) Int. Cl.
| | | |
|---|---|---|
| *A61F 13/00* | (2006.01) | |
| *A61K 9/70* | (2006.01) | |
| *A61L 15/18* | (2006.01) | |
| *A61L 15/16* | (2006.01) | |
| *A61L 15/08* | (2006.01) | |

(52) U.S. Cl.
USPC ........... 424/443; 424/444; 424/445; 424/447; 424/448; 604/304

(58) Field of Classification Search
USPC .......... 514/183; 424/443, 444, 445, 446, 447, 424/448; 604/304
See application file for complete search history.

(56) References Cited

U.S. PATENT DOCUMENTS

| | | | |
|---|---|---|---|
| 4,148,875 A * | 4/1979 | Barnett et al. ............. | 514/772.6 |
| 4,504,395 A * | 3/1985 | Harpel et al. ................ | 210/712 |
| 4,822,349 A | 4/1989 | Hursey et al. | |
| 5,056,510 A | 10/1991 | Gilman | |
| 5,429,591 A | 7/1995 | Yamamoto et al. | |
| 5,478,308 A | 12/1995 | Cartmell et al. | |
| 5,800,372 A | 9/1998 | Bell et al. | |
| 5,891,078 A | 4/1999 | Turngren et al. | |
| 5,899,871 A | 5/1999 | Cartmell et al. | |
| 5,935,091 A | 8/1999 | Friedman | |
| 5,944,933 A | 8/1999 | Heller et al. | |
| 6,007,837 A | 12/1999 | Enscore et al. | |
| 6,060,461 A | 5/2000 | Drake | |
| 6,114,594 A | 9/2000 | Barikosky | |
| 6,521,265 B1 | 2/2003 | Patterson | |
| 6,568,398 B2 | 5/2003 | Cohen | |
| 6,580,011 B1 | 6/2003 | Jennings-Spring | |
| 6,897,348 B2 | 5/2005 | Malik | |
| 6,998,510 B2 | 2/2006 | Buckman et al. | |
| 2002/0120241 A1* | 8/2002 | Tyrrell et al. .................. | 604/364 |
| 2003/0008011 A1* | 1/2003 | Mershon ....................... | 424/487 |
| 2003/0109820 A1 | 6/2003 | Gross et al. | |
| 2003/0133990 A1 | 7/2003 | Hursey et al. | |
| 2003/0176828 A1 | 9/2003 | Buckman et al. | |
| 2004/0193088 A1 | 9/2004 | Looney et al. | |
| 2005/0277577 A1 | 12/2005 | Hunter et al. | |
| 2006/0002976 A1 | 1/2006 | Kronenthal | |
| 2006/0015235 A1 | 1/2006 | Ringger et al. | |
| 2006/0155235 A1 | 7/2006 | Sawyer | |
| 2007/0160638 A1 | 7/2007 | Mentkow et al. | |
| 2008/0125686 A1 | 5/2008 | Lo | |
| 2008/0167593 A1 | 7/2008 | Fleischmann | |

FOREIGN PATENT DOCUMENTS

| | | |
|---|---|---|
| WO | 9959647 A1 | 11/1999 |
| WO | 2006088912 A2 | 8/2006 |
| WO | 2007081760 A2 | 7/2007 |

OTHER PUBLICATIONS

HEMCON: "The Remarkable Hemcon Bandage is Designed to Control Severe Bleeding and Save Lives" http://www.hencom.com/home.html, 2004.
International Search Report dated Nov. 8, 2010.

* cited by examiner

*Primary Examiner* — Ernst Arnold
(74) *Attorney, Agent, or Firm* — Laurence A. Greenberg; Werner H. Stemer; Ralph E. Locher

(57) ABSTRACT

A hemostatic agent composition, delivery system and method include a hemostatic agent composition which is inert and non-reactive relative to blood clotting proteins and platelets. The composition includes a clay material combined with a humectant in a stable suspension embedded in a mesh fabric and, when dried, is capable of accelerating the formation of a stable clot when applied to an actively bleeding wound or drying other bodily fluids.

13 Claims, 2 Drawing Sheets

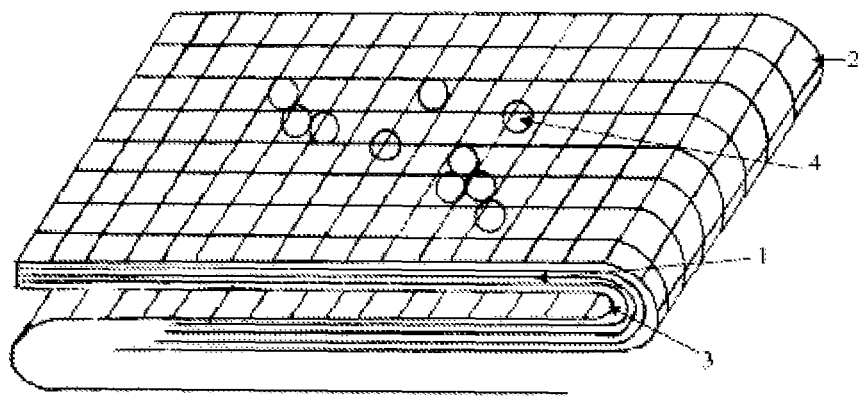
FIG. 1
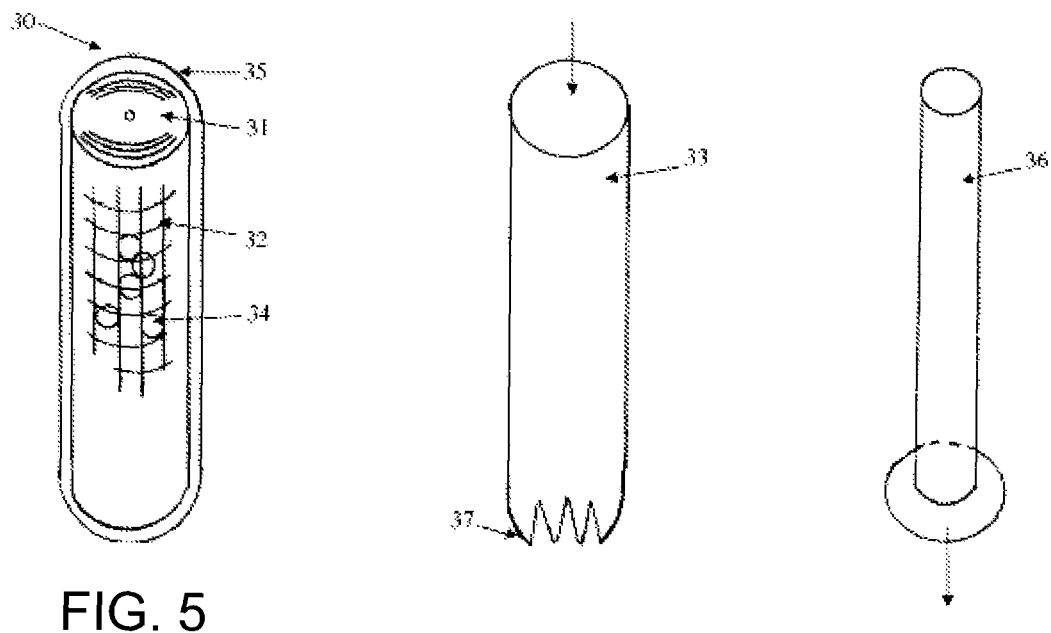
FIG. 5
FIG. 6
FIG. 7

HEMOSTATIC AGENT COMPOSITION, DELIVERY SYSTEM AND METHOD

CROSS-REFERENCE TO RELATED APPLICATIONS

This application is a Continuation-In-Part of U.S. patent application Ser. No. 12/191,323, filed Aug. 14, 2008 which claims the priority under 35 U.S.C. 119(e) of U.S. Provisional Patent Application No. 60/964,955, filed Aug. 16, 2007, which is a Continuation-In-Part of U.S. patent application Ser. No. 11/453,524, filed Jun. 15, 2006 which claims the priority under 35 U.S.C. 119(e) of U.S. Provisional Patent Application No. 60/757,459, filed Jan. 9, 2006 and this application also claims the priority under 35 U.S.C. 119(e) of U.S. Provisional Patent Application Nos. 61/158,169, 61/158,188 and 61/158,193, all filed Mar. 6, 2009, the disclosures of which are incorporated herein by reference in their entirety.

BACKGROUND OF THE INVENTION

1. Field of the Invention

The present invention relates to a hemostatic agent composition, delivery system and method. This composition, delivery system and method may be used to deliver a hemostatic agent directly proximate a hemorrhage site and may also be used to dry oozing fluid sites while keeping an area moist preventing re-irritation, such as by bed sores.

More specifically, the invention includes a system for delivering a hemostatic agent to a wound, a hemostatic agent composition, a method of accelerating blood clotting of a wound, a hemostatic agent and delivery system, a bandage to be applied to a wound, oozing blood or other bodily fluids and a bandage to be applied to a narrow wound opening oozing blood or other bodily fluids.

2. Description of Related Art

It has long been known that injuries which result in excessive bleeding if not quickly or properly addressed can often prove fatal. Unfortunately, this fact is well supported by data gathered during numerous armed conflicts throughout time. For instance, it has been reported that over 2,500 soldiers died from extremity wounds during the Vietnam War solely because they bled to death. Military data also indicate that approximately 50% of combat casualties die from bleeding, and that the majority die within thirty minutes of the injury. It has also been reported that of the fifty %, approximately sixty % die within the first five minutes while the remaining persons die within one hour if not properly treated.

In addition, it has been estimated that there are over seventy million emergency room visits each year for bleeding. As above, with respect to injuries sustained during battle, bleeding or acute hemorrhaging is a leading cause of death in trauma cases among the civilian population.

As such, it is clear that rapid and effective control of hemorrhaging saves lives. Attempts to address the need for such rapid and effective hemorrhage control have resulted in a development of a number of so called hemostatic bandages and other products purported to facilitate rapid control of bleeding.

One such product includes a granular zeolite material which may be obtained from volcanic lava rocks. This material is placed into a bleeding wound where it absorbs water molecules from the blood, thereby creating a high platelet concentration which promotes clotting. However, it has been documented that the absorption process affected by this zeolite is a highly exothermic reaction which generates a considerable amount of heat, attributable to reaction with the iron content of the zeolite. More specifically, temperatures ranging from 90° C. to 100° C. have been reported following use of the material, causing second degree burns to soldiers injured and treated with this product in Iraq, as well as to those persons administering the product, even though personnel administering this product must be trained and certified to administer the same.

A further drawback to this product is that the zeolite material is packaged to be simply poured on to an open wound, however, in the case of hemorrhaging of any significance, such as may occur due to laceration of a major artery, the pressure of blood exiting the wound will simply cause the material to be dispersed thereby minimizing and/or eliminating the effectiveness of the clotting properties therein. Another disadvantage is that the zeolite's efficacy is exhausted at first contact with blood such that a clot may be formed distant to the actual wound source without stopping hemorrhaging. Yet another disadvantage of this product is that the zeolite material is granular in nature, making it difficult to subsequently remove the material from the wound via normal measures such as irrigation and/or suctioning of the wound area, once the injured person is transferred to an operating room or other such treatment facility.

Another product is made from chitosan, which is derived from the exoskeletons of shellfish. Reports as to the effectiveness of this device in hemorrhage control are conflicting, in particular, its effectiveness in the event of hypothermia in the patient, such as may occur from shock following significant blood loss, is reported to be severely reduced or diminished. In addition, there have been reports of the device being improperly applied, e.g., the wound is not contacted by the active surface due to the device being placed into the wound site upside down. Since this product is derived from living organisms, it has an extremely limited shelf life during which time it must either be utilized or disposed of, and given the significant cost of each unit, this is a further considerable disadvantage. This product is available in powder form or adhered to a felt material.

Another type of hemostatic bandage is manufactured from single cell algae and includes poly-N-acetylglucosamine. This device is structured to enable persons with minimal training to quickly and effectively control and/or stop hemorrhaging from extremity trauma. More in particular, when the material comes in contact with blood it reportedly stimulates platelet aggregation and activation which causes the body to secrete tromboxane, which stimulates the blood vessels to constrict in the vicinity of the wound. Stated differently, the poly-N-acetylglucosamine material acts as a catalyst to accelerate the normal clotting process thereby accelerating the bodies' own control of the bleeding. Once again, since this product is derived from living organisms, it has a limited shelf life during which it must be utilized or disposed. Further, its effectiveness in the event of hypothermia in the patient, such as in the above example, is questionable.

Another material which is structured to be applied, i.e., poured, directly to wounds has been synthesized from potato starch. Reportedly, the particles accelerate natural clotting by concentrating blood solids forming a gel around the same so as to promote clotting. In particular, the larger particles of the blood components are concentrated on the surface of the synthesized potato starch product, thereby promoting accelerated clotting. As noted, this material is also in a powder form and has been applied directly to a bleeding wound with a bellows type applicator as noted above with respect to the zeolite material, however, in the event of excessive bleeding such as a major artery, the pressure of the blood flowing from the wound is often sufficient to disperse the powder thereby once again, minimizing or eliminating the clotting property exhibited therein, even though the wound site is to be covered with a standard bandage and pressure applied after treatment with the synthesized potato starch material.

Yet another powdered material is composed from a hydrophilic polymer and a potassium salt in combination with a bovine based thrombin material. This powder is also reported to stop bleeding on contact based upon studies for various minor wounds, in which no covering bandage is required, however, as noted above with respect to the other "pour" type products, in the event of any significant bleeding, the blood pressure itself is likely to disperse the product, thereby reducing or eliminating any hemostasis it was intended to effect.

One product patented from TraumaCure (Bethesda, Md.) is a balloon device. A deflated balloon is inserted through the wound entry point and then inflated while in the wound cavity, putting pressure against the wound walls and source of bleeding.

Another type of hemostatic bandage is manufactured using a low absorption, low swell clay material, kaolin, disposed on one side of a substrate of felt material adhered using a polyol binder. Several drawbacks exist with this product including the use of a low absorption clay material which severely limits its speed and capacity in promoting clotting in major arterial bleeding wherein time is critical in terminating hemorrhaging. Due to the low absorption capacity and its tight weave substrate, its efficacy is exhausted at first contact with blood such that a clot may be formed distant to the actual wound source without stopping hemorrhaging. Kaolin molecules swell at first contact with blood creating an impenetrable barrier to further absorption. The clay also does not contain a beneficiating agent such as a dispersal agent to optimize absorption. Additionally, the tight weave of the felt-like fabric which is required because of the limitations of its adhesion capability restrict even further the amount of clay material able to be disposed on it. In addition, the end product created by the disposition of the kaolin on this felt-like material creates a very stiff fabric which does not easily form to the wound irregularities. The stiff fabric does not allow for insertion into narrow wound openings. The closed weave fabric does not allow for percolation of the water content of the blood through the fabric layers further limiting efficacy.

BRIEF SUMMARY OF THE INVENTION

It is accordingly an object of the invention to provide a hemostatic agent composition, delivery system and method, which overcome the herein aforementioned disadvantages of the heretofore-known devices and methods of this general type and which provide a system for rapid, effective, and efficient control of hemorrhaging including hemorrhaging of major arteries, which may be quickly and properly applied by personnel with minimal training.

Medical and non-medical personnel alike are familiar with basic hemorrhage control procedure which entails packing an open weave gauze material (by way of example, Kendall, Kerlix bandage roll) into the wound and holding pressure as well as subsequently applying a pressure bandage. It would be beneficial to provide a system or systems which contain all of these elements in addition to being easily removed without adversely affecting the clot as well as provide exceptional clot stability to allow for transport of the patient without rebleeding. Further, it would be particularly beneficial to be able to apply the bandage, packaged in a roll form, using one hand in order to allow for self-administering. More in particular, it would be beneficial to provide a system for delivering an effective amount of a hemostatic agent directly to a wound site, as well as providing a mechanism to maintain an effective amount of the hemostatic agent at the wound site to control bleeding. Also, it would be advantageous for such a system to include a hemostatic agent which is substantially nonreactive and hypoallergenic when applied to a wound. Further, the hemostatic agent employed in such a system should promote clotting of the blood in a non-reactive manner, i.e., without exothermic reaction with the blood and the localized temperature increase associated therewith. Yet another advantage may be realized by providing such a system with a hemostatic agent which is inorganic, thereby benefiting from a substantially indefinite shelf life.

With the foregoing and other objects in view there is provided, in accordance with the invention, a system for delivering a hemostatic agent to a wound. The system comprises a composition of a hemostatic clay material combined with a glycol humectant in a stable suspension unaffected by variations in temperature, the glycol humectant in the stable suspension acting to create a hydrophilic matrix, and an absorbent mesh fabric having the composition embedded therein to adhere to the wound, permit at least some of the composition to come into contact with a bleeding source, effect hemostasis of bleeding, accelerate stable clotting, prevent displacement of the composition by arterial pressure and be easily removed, the stable suspension allowing for increased embedment in the mesh fabric matrix and acting to create elasticity providing wound conformation.

The hemostatic agent composition and delivery system are structured to deliver a hemostatic agent composition directly to a hemorrhage site, for example a lacerated artery, so as to facilitate clotting of the blood and terminate hemorrhaging at the site. As such, the hemostatic agent delivery system of the present invention is further structured to concentrate and retain the hemostatic agent at the hemorrhage site, once again, to facilitate clotting and terminate hemorrhaging. The composition of the present invention is easily and economically manufactured and priced accordingly, affording the consumer and general public greater access to these life saving inventions.

In accordance with another feature of the invention, the hemostatic clay material includes a smectite clay, in particular a hectorite clay, in which 95% of the hectorite in the hectorite clay has a particle size of less than 76 microns.

In accordance with a further feature of the invention, the hectorite clay is beneficiated with an addition of a dispersal agent and by a reduction of its ferric and ferrous oxide content, and the composition absorbs a weight of liquid greater than a weight of the composition.

In accordance with an added feature of the invention, the composition absorbs a weight of liquid more than twenty four times a weight of the composition and the composition absorbs a weight of liquid more than eight times greater than a weight of the composition in approximately one minute or less.

In accordance with an additional feature of the invention, the composition is inert relative to blood clotting proteins, blood platelets, extrinsic blood clotting mechanisms and intrinsic blood clotting mechanisms, and the absorbent mesh fabric is configured to apply the composition directly to an external wound.

With the objects of the invention in view, there is also provided a hemostatic agent composition, comprising 40-70% propylene glycol, 20-40% hectorite clay, 5-15% $H_2O$, 1-10% Carbomer, and 1-10% triethanolamine. In the composition, preferably, the propylene glycol percentage is 55.56%, the hectorite clay percentage is 27.78%, the $H_2O$ percentage is 8.34%, the carbomer percentage is 4.17%, the triethanolamine percentage is 4.17% and the composition exhibits a kinematic viscosity of more than 100,000 cps.

With the objects of the invention in view, there is additionally provided a method of accelerating blood clotting of a wound. The method comprises locating a wound, providing a hemostatic agent composition having at least one smectite clay, and applying the composition into the wound.

In accordance with another mode of the invention, the wound is an internal wound not being readily visible or locatable from outside a patient, the smectite clay is hectorite, the step of applying the composition is carried out from a support member, and, after clotting, the application site of the hemostatic agent composition is irrigated to remove substantially all of the hemostatic agent composition.

With the objects of the invention in view, there is furthermore provided a hemostatic agent and delivery system, comprising at least one hemostatic agent for facilitating blood clotting, and a delivery assembly for permitting disposition of an amount of the hemostatic agent proximate a hemorrhage site. The delivery assembly at least temporarily retains the amount of the hemostatic agent for release upon disposition proximate to the hemorrhage site.

In accordance with another feature of the invention, the delivery assembly is dehydrated and includes a support member for at least temporarily retaining the amount of the hemostatic agent, and the hemostatic agent is formed of a hectorite clay alone or in combination with other water absorbing materials and absorbs body fluids or promotes clotting.

In accordance with a further feature of the invention, the delivery assembly includes a release member with a soluble material fabricated from a hydrophilic material for dissolving and releasing the amount of the hemostatic agent upon disposition proximate to the hemorrhage site while providing secondary hemostasis and wound occlusion, the release member dissolves at the hemorrhage site, the release member includes a film formed or placed over the hemostatic agent, and the release member is selected from the group consisting of polyvinyl alcohol, glycerol, methyl cellulose and starch.

In accordance with an added feature of the invention, the delivery assembly permits disposition of the amount of the hemostatic agent proximate the hemorrhage site by one hand of a user, such as by administration of the hemostatic agent with a support member containing the hemostatic agent.

In accordance with an additional feature of the invention, other materials are to be added to the hemostatic agent to provide ancillary benefits to clotting or fluid absorbing functions of the hemostatic agent. The other materials include antiseptics, analgesics, antibiotics, anti-fungals, antimicrobials, anti-inflammatories, antihistamines, silver or copper ion compounds. The materials may be pharmaceutical or botanical in nature.

In accordance with another feature of the invention, the delivery assembly includes a mesh fabric containing an open weave matrix to allow for retention of large amounts of the hemostatic agent. The mesh fabric is flexible to allow it to conform to a shape of a wound and to allow it to be folded. The at least one hemostatic agent includes a clay material combined with a carbomer or a combination of carbomers and a humectant chosen from the group consisting of polyols or propylene glycol alone or in combination with another humectant in a stable suspension and embedded in the mesh fabric.

With the objects of the invention in view, there is also provided a bandage to be applied to a wound, oozing blood or other bodily fluids. The bandage comprises a flexible support member, a mesh fabric mounted on the flexible support member, and a hectorite clay material combined with propylene glycol in a stable suspension in a dehydrated form and embedded in the mesh fabric. The clay material accelerates clotting upon contact with blood or promotes drying upon contact with bodily fluids.

In accordance with another feature of the invention, a soluble film is formed or placed over the clay-embedded mesh fabric, and a handle or other stiff retentive member is attached to the flexible elastic support member on a side opposite the clay-embedded mesh fabric. The flexible support member is a flexible adhesive support member for adhering to the skin of a patient or a flexible elastic support member configured to exert and retain pressure on a wound site.

With the objects of the invention in view, there is additionally provided an alternative bandage to be applied to a narrow wound opening oozing blood or other bodily fluids. The bandage comprises a cylindrical mesh fabric, and a hectorite clay combined with propylene glycol in a stable suspension in a dehydrated form and embedded in the mesh fabric, the clay material accelerating clotting upon contact with blood or promoting drying upon contact with bodily fluids.

In accordance with a further feature of the invention, a soluble film is formed or placed over the clay-embedded mesh fabric, and an applicator is used for applying the clay-embedded mesh fabric proximate a wound site.

In accordance with a concomitant feature of the invention, the applicator includes a barrel surrounding the clay-embedded mesh fabric and a plunger for ejecting the clay-embedded mesh fabric from the barrel into a wound.

At least one embodiment of the delivery system of the present invention includes at least one hemostatic agent composition structured to facilitate blood clotting. More in particular, at least one hemostatic agent of the present invention comprises a smectite clay material. In at least one further embodiment, a beneficiated hectorite clay is utilized as the hemostatic agent. The present invention encompasses the utilization of a clay material as a hemostatic agent either alone or in combination with one or more additives, as is discussed further below.

To facilitate delivery of the hemostatic agent to a hemorrhage site, the delivery system of the present invention further comprises a delivery assembly which is structured to at least temporarily contain an amount of the hemostatic agent, at least until the agent is delivered proximate to a hemorrhage site. The assembly is defined by a multi-layered material wherein the application of the device to a hemorrhage site causes the hemostatic agent to come in contact with the blood rapidly terminating bleeding. This result is caused by the combination of the open weave design of the material and the wicking action of both the material and the hemostatic composition.

The delivery assembly, in at least one embodiment, includes a support member disposed in overlying relation to the hemostatic agent comprising a multilayered material matrix impregnated with the hemostatic agent. By way of example only, this embodiment may be applied using a tampon type applicator to insert into narrow wound openings.

The delivery assembly, in at least one embodiment, includes a release member disposed in overlying relation to a support member. More in particular, the release member and the support member are cooperatively structured to at least temporarily contain the hemostatic agent therebetween, the release member and the support member being attached about their respective peripheries.

The delivery assembly, in at least one embodiment, includes a release member surrounding the hemostatic agent, with the release member comprising a soluble material structured to at least partially dissolve and release the hemostatic agent upon disposition directly proximate to a hemorrhage site. By way of example only, this embodiment may be applied using a tampon type applicator to access narrow wound openings.

In order to achieve releasable containment of one or more hemostatic agents via the delivery assembly of the present invention, the release member comprises a soluble material structured to at least partially dissolve and release the hemostatic agent upon disposition directly proximate to a hemorrhage site. In at least one embodiment, the release member comprises a soluble polymeric material, such as, by way of example only, a polyvinyl alcohol material.

To further facilitate delivery of an amount of a hemostatic agent directly to a hemorrhage site, the delivery assembly of the present invention may also include a handle member attached to an outer surface of the support member, wherein the handle member is structured to facilitate handling of the delivery system by a user. At least one embodiment of the present invention includes a handle member having a visual indication to facilitate location or identification of the handle member by a user. This feature may prove critical in the hectic and often chaotic environment in which the hemostatic delivery system of the present invention is utilized, such as, on the battle field, field medical unit, or hospital emergency room.

The present invention further encompasses a method of application of a hemostatic agent to a hemorrhage site including the step of delivery of an amount of a hemostatic agent, wherein the hemostatic agent comprises a beneficiated hectorite clay material, directly proximate the hemorrhage site. The method further includes concentrating the amount of hemostatic agent in a substantially conforming relation to the configuration of the hemorrhage site, and retaining the amount of the hemostatic agent at the hemorrhage site in a substantially occluding relation so as to facilitate clotting and terminate hemorrhaging at the site. This is achieved through the binding of the propylene glycol to the clay molecules with the addition of specific carbomers in a stable suspension impregnated through the multiple layers of material and then dehydrated. This embodiment, when rehydrated through contact with blood, becomes a contiguous material rather than a particulate one which might otherwise cause the clay material to migrate and potentially cause ancillary damage in other areas as well as make it difficult to completely remove from the wound. As a result, no additional irrigation and suction procedures are required to remove the material from the wound. As noted above, the hemostatic agent of the present invention is structured to form a stable clot such that the patient may be moved, once hemorrhaging has been effected. Another advantage of the use of this stable suspension is its adhesive properties (see adhesive testing chart) which allows the device to completely occlude the hemorrhage site adhering to it even against the pressure of major arterial bleeding.

An additional advantage is that the embodiments are unaffected by variations in temperature. They do not become less pliant, and the active ingredient retains its efficacy. In addition, no separation occurs in the hemostatic agent composition.

An additional advantage of this stable suspension is that it allows for the retention of a greater volume of the hemostatic agent such that even when dehydrated and folded, the hemostatic agent remains bound to the multi layered gauze while remaining pliant and foldable. The adhesive property of the stable suspension allows for Z-folding the product rather than providing it in a rolled form which requires unreeling prior to application thereby causing contamination. This Z-fold design permits the medical care giver to avoid contamination and save critical time when applying the device.

The ability of the gauze (UltraClot Gauze) of the invention to retain the hemostatic agent composition is illustrated by the following table:

| Product | Hole size (mm)* | Hole spacing (mm)* | Weight fabric (gr)* | Weight of Hemostatic agent (gr)* | % of hemostatic agent (gr)* |
|---|---|---|---|---|---|
| UltraClot Gauze | 3.0-5.0 | 0.12 | 40 | 108 | 270% |
| Celox Gauze | <0.1 | n/a | 35 | 18 | 50% |
| Combat Gauze | 0.5-1.0 | 1.5 | 12 | 6 | 50% |

*All measurements are approximate.

This table shows the retention of the ingredients in the gauze/fabric of UltraClot Gauze according to the invention, Celox Gauze (Medtrade), and Combat Gauze (Z-Medica). The UltraClot Gauze holds 270% of the hemostatic agent relative to the weight of the gauze as compared to 50% for the other products. This is due to the larger hole size and more proximate spacing of the holes in the UltraClot Gauze.

All of these embodiments also allow for use in instances of oozing fluid sites where the need exists to dry and remove excess fluid while keeping the area moist and promoting healing.

Other features which are considered as characteristic for the invention are set forth in the appended claims.

Although the invention is illustrated and described herein as embodied in a hemostatic agent composition, delivery system and method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a diagrammatic, perspective view of a Z-fold, multilayered gauze in which a hemostatic composition has been embedded according to the invention;

FIGS. 5, 6 and 7 are perspective views of a plug having the gauze of the invention rolled therein, an applicator for the plug and a plunger for the applicator.

DETAILED DESCRIPTION OF THE INVENTION

Referring now to the figures of the drawings in detail and first, particularly, to FIG. 1 thereof, there is seen a first embodiment of the hemostatic agent composition delivery system according to the present invention having a multilayered gauze 1 formed of an open weave mesh fabric 2 formed with a Z-fold 3. A hemostatic composition 4 has been embedded in the gauze 1.

Figure 2:
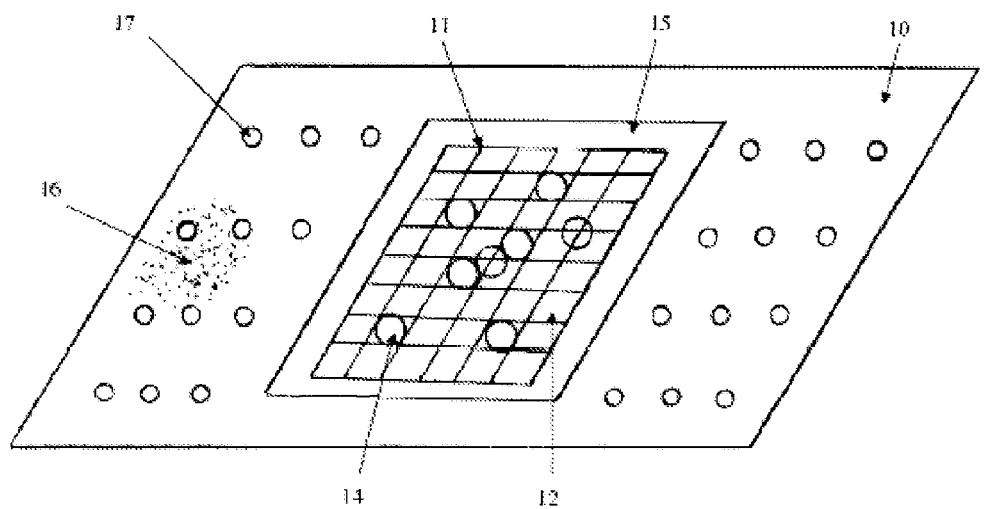
FIG. 2 is a perspective view of an adhesive bandage having the gauze of the invention.

A second embodiment of the hemostatic agent composition delivery system according to the present invention, as seen in FIG. 2, is in the form of an adhesive bandage having a flexible support member 10 with a gauze 11. The gauze 11 is in the form of an open weave mesh fabric 12 with an embedded hemostatic composition 14. A polymeric material release member or film 15, which may be formed of PVA (polyvinyl alcohol), covers the open weave mesh fabric 12 having the hemostatic composition 14. An adhesive 16 is applied to the entire area of the flexible support member or adhesive bandage 10 to adhere to the skin near a wound, although only a portion of the adhesive is shown for the sake of clarity. The flexible support member or adhesive bandage 10 also has moisture relief holes 17 formed therein. Elements 10, 11, 12, 15 form a delivery assembly for the hemostatic composition 14.

Figure 3:
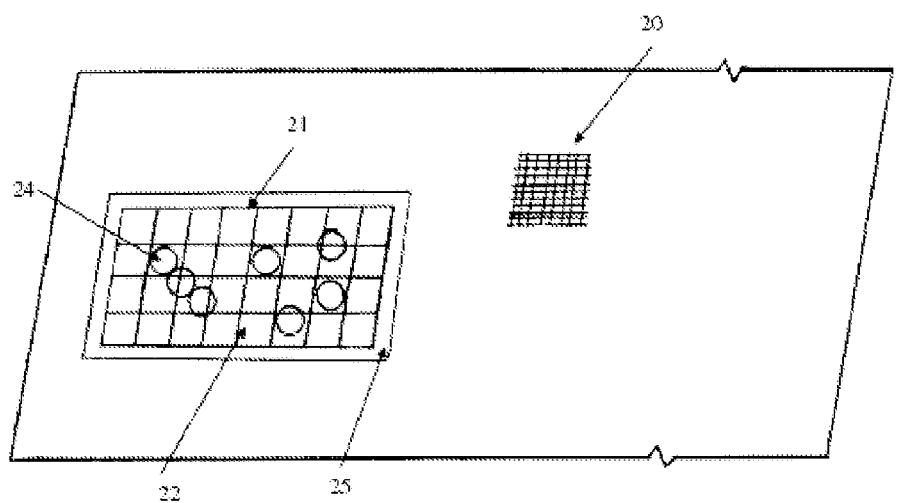
FIG. 3 is a perspective view of a compression bandage having the gauze of the invention.
Figure 4:
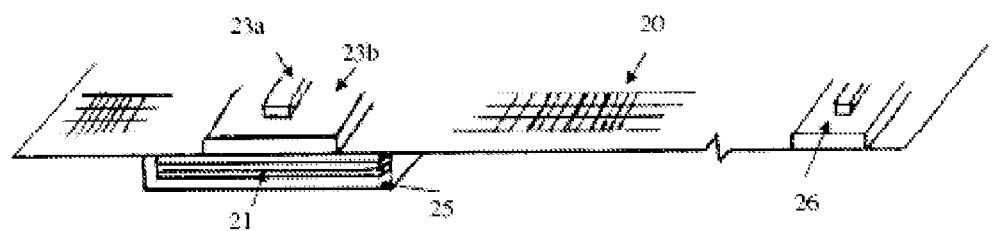
FIG. 4 is a fragmentary, perspective view of a compression bandage having the gauze of the invention.

FIGS. 3 and 4 show a third embodiment of the hemostatic agent composition delivery system according to the present invention, in the form of a flexible support member or elastic compression bandage 20, the material of which is only shown in a small area for clarity, but is actually used throughout. A gauze 21 in the form of an open weave mesh fabric 22 with an embedded hemostatic composition 24, is disposed on one side of the flexible support member or elastic compression bandage 20. A PVA (polyvinyl alcohol) release member or film 25 covers the open weave mesh fabric 22. While FIG. 3 shows a first, lower side of the flexible support member or elastic compression bandage 20 which faces towards and is applied to the skin over a wound, FIG. 4 shows a second, opposite, upper side of the flexible support member or elastic compression bandage 20, which faces away from the skin in use. A compression securing handle 23a with a base 23b, is applied to the second, upper side of the flexible support member or elastic compression bandage 20, opposite the gauze 21, in order to manually position the gauze over the wound. A compression locking device 26 serves the purpose of locking the flexible support member elastic compression bandage 20 in place. Elements 20, 21, 22, 25 form a delivery assembly for the hemostatic composition 24.

A fourth embodiment of the hemostatic agent composition delivery system according to the present invention, in the form of a plug 30, is shown in FIGS. 5, 6 and 7. The plug 30 has a tightly-rolled, cylindrical gauze 31 in the form of an open weave mesh fabric 32 having an embedded hemostatic composition 34. A PVA (polyvinyl alcohol) release member or film 35 covers the rolled open weave mesh fabric 32. A tampon-type applicator barrel 33, with a slotted edge 37, is shown in FIG. 6. The applicator barrel 33 is slid over the plug 30 and a tampon-type applicator plunger 36 shown in FIG. 7 is pushed through the barrel 33 in the direction of the arrows, in order to insert the gauze 31 into a wound. Elements 30, 31, 32, 35 form a delivery assembly for the hemostatic composition 34.

Details of the hemostatic agent composition delivery system according to the present invention and its structure used to facilitate delivery of a hemostatic agent directly proximate a hemorrhage site, will be explained in detail below. More in particular, the present invention is directed towards a hemostatic agent delivery system shown in FIGS. 1-7 which may be quickly and effectively utilized to facilitate clotting and to control and/or terminate hemorrhaging of an injured person, such as, a soldier wounded on a battle field, by personnel with minimal training. As will become apparent from the following, the hemostatic agent delivery system of the present invention is structured such that personnel with minimal instruction in its use will be able to readily identify the proper orientation of the delivery assembly, so as to facilitate disposition of the delivery assembly directly proximate a hemorrhage site.

In order to reduce and/or terminate excessive bleeding at a hemorrhage site, the hemostatic agent delivery system of the present invention includes at least one hemostatic agent composition 4, 14, 24, 34. Of course, it is within the scope and intent of the present invention to include a plurality of hemostatic agents, or a combination of one or more hemostatic agent and one or more additives, such as may be desirable to enhance the performance of one or more hemostatic agent. As one example, the hemostatic agent of the present invention, in at least one embodiment, includes a hydroxyethyl cellulose additive structured to enhance the absorption of water from the blood by the hemostatic agent, thereby increasing the rate of clot formation, and termination of the hemorrhage. As noted above, bleeding is a major cause of death in both military and civilian injuries, and the present invention enables quick and effective control and/or termination of hemorrhaging, which is proven to save lives.

In at least one embodiment of the present invention, at least one hemostatic agent includes smectite clay. Smectite is a family of naturally occurring layered swelling clays which include bentonite, also known as montmorillonite, hectorite, and saponite. Kaolinite, a related clay, is less absorbent and swelling than the aforementioned. More in particular, the smectite clays are layered silicates which swell in water, and are widely used as rheological additives. Specifically, the silicate platelets include three layers, two silicate dioxide layers which embed a metal oxide layer. In bentonite clays, the metal oxide layer is mainly aluminum, whereas in hectorite clay the metal oxide layer includes magnesium. More importantly, bentonite may include approximately 4% by weight of ferric and ferrous oxides, hectorite clay is substantially iron free, including generally less than one-half of one percent (<0.50%) by weight. This is important, as a presence of iron is believed to promote exothermic reactions between hemostatic agents and body fluids during absorption processes. When purified and ground, the surface contact area of an identical particle size of hectorite clay contains 10 times the surface contact area as that of bentonite clays and 20 times that of kaolin clays. A further benefit of hectorite clay, for use in conjunction with the present invention, is that it can be highly beneficiated.

One preferred embodiment of the present invention includes a beneficiated hectorite clay as a hemostatic agent composition 4, 14, 24, 34. More in particular, the present invention may include Bentone EW® which is a highly beneficiated hectorite clay available from Elementis Specialties of Hightstown, N.J. Bentone EW® has a density of about 2.5 grams per cubic centimeters (g/cm.sup.3) and, more importantly, a particle size distribution wherein approximately 94% or greater of the material is less than 200 mesh screen size. In addition, this beneficiation includes, but is not limited to, a dispersal agent to significantly increase the capacity and speed at which water is absorbed through the various layers of the hectorite by increasing the wicking action through the strata of the hemostatic agent, preventing the creation of an impenetrable barrier caused by the swelling of the clay molecules where water and clay first meet. Additionally, in Bentone EW®, the ferric and ferrous oxide content of the clay is further reduced, eliminating any exothermic reaction.

Other materials may be added to the hemostatic agent composition in order to provide ancillary benefits to the clotting or fluid absorbing functions of the hemostatic formula including, but not limited to, antiseptics, analgesics, antibiotics, anti-fungals, antimicrobials, anti-inflammatories, antihistamines, silver, or copper ion compounds, etc., whether pharmaceutical or botanical in nature.

Of course, as noted above, the present invention includes a hemostatic agent delivery system shown in FIGS. 1-7 including a plurality of hemostatic agents in the composition 4, 14, 24, 34, as one example, a combination of hectorite and bentonite clays in a variety of proportions. Also as noted above, one or more additives may be combined with the hemostatic agent to enhance the hemostatic properties thereof. As just one example, in one further preferred embodiment of the present invention the hemostatic agent includes a highly beneficiated hectorite clay in combination with a hydroxyethyl cellulose additives. More in particular, the hemostatic agent of one preferred embodiment includes Bentone LT® once again, available from Elementis Specialties.

An important consideration for selection of the hemostatic agent for use in the present invention is that the agent be substantially inert and non-reactive when disposed in contact with an open wound, and the blood or other body fluids being released therefrom. More in particular, as noted above, the hectorite clays do not include iron components to any significant degree therefore they are substantially non exothermic upon contact with water, blood, or other aqueous or bodily fluids. In addition, because of the powdered physical configuration of beneficiated hectorite clay, it serves to aid in the formation of a stable clot upon application to a hemorrhage site. Specifically, Bentone EW® is purified and processed into a fine powder in the beneficiating process thereby increasing the effective surface area of the material, and resulting in an increase in absorptive capacity and speed for removing the water content of blood so as to concentrate the blood platelets to facilitate clotting and to form a stable clot at the hemorrhage site. In tests conducted on swine, stable clots were formed at a hemorrhage site formed of a lacerated femoral artery utilizing the hemostatic agent delivery system and hemostatic agent in accordance with the present invention.

The hemostatic delivery system of the present invention, as shown in FIGS. 1-7, includes a delivery assembly which is structured to facilitate disposition of an amount of a hemostatic agent in the composition 4, 14, 24, 34 directly proximate a hemorrhage site.

In one preferred embodiment shown in FIG. 1, the clay material is smectite clay, more particularly, hectorite, beneficiated to increase absorption speed and capacity. This preferred hectorite clay is Bentone EW® from Elementis Specialties, Hightstown, N.J. The beneficiation includes uniform particle size to less than 200 screen mesh, the addition of a dispersal agent, and further reduction of ferric and ferrous oxide content. In order to achieve a stable suspension of the clay in a slurry form, propylene glycol, a humectant, is used in combination with specific carbomers into which the clay material is then thoroughly blended to create a uniform mixture which is totally unaffected by cold or heat. This mixture is then thoroughly impregnated through all the layers of an open weave mesh fabric 2 of a highly absorbent gauze 1, by way of example only, a Kendall Kerlix 6-ply bandage roll, and run through a set of rollers or other equipment to thoroughly embed the suspension in the gauze and achieve uniform thickness. This is then dried using a dehydrating heat tunnel or other method and then given a Z-fold 3 and placed into a sealed package.

In another embodiment shown in FIG. 2, a delivery assembly having a gauze 11 impregnated with the hemostatic composition 14 may be combined with a flexible support member 10 that may be applied to the healthy tissue surrounding the wound and kept in place using, by way of example only, a flexible backing with adhesive 16. The gauze 11 of the delivery assembly may be sewn, glued, or otherwise mounted to the flexible support member 10 of the adhesive bandage.

In another embodiment shown in FIGS. 3 and 4, the support member may be an elastic support member or compression bandage 20 that may be applied to the wound and, by way of example only, is constructed to retain its position without releasing pressure. The open weave mesh fabric 22 of a gauze 21 with a hemostatic composition 24 embedded therein may be sewn, glued, or otherwise mounted to the delivery assembly. The delivery assembly may include a handle member 23a with a base 23b that is placed on the backside of the elastic support member 20. The handle 23a serves several purposes, the first of which being to facilitate disposition of the delivery assembly directly proximate to a hemorrhage site, facilitating delivery of the hemostatic agent thereto. More in particular, the handle is structured and configured to be grasped by one hand of a user and allow the user to quickly and effectively position the delivery assembly including the hemostatic agent with the elastic support member directly onto a hemorrhage site, such as, a lacerated artery. In addition, the handle may be constructed of a stiff material allowing the medical care giver to exert greater pressure directly on the hemorrhage site. The handle also prevents premature release of the hemostatic agent by avoiding contact of the medical care giver's wet hands with the PVA film release member. The handle member may be included of a visual indication to facilitate location of the handle member by a user. More in particular, the visual indication may include indicia such as lettering, symbols, stripes, etc., applied directly onto the handle member or may include a color contrast between the support member and the handle which may be a bright color or color pattern.

The hemostatic delivery system of the present invention further includes a delivery assembly which is structured to facilitate disposition of an amount of a hemostatic agent directly proximate a hemorrhage site. More in particular, the delivery assembly shown in FIGS. 2-5 is structured to releasably contain an amount of the hemostatic agent for delivery to a hemorrhage site, by way of example only, PVA or polyvinyl alcohol film 15, 25, 35.

The release member or film 15, 25, 35 includes a soluble material of construction, by way of example only, a polymeric material such as polyvinyl alcohol, which is structured to at least partially dissolve upon contact with an aqueous solution, such as blood or other bodily fluids discharging from a wound, thereby creating a hermetic seal around the wound. This hermetic seal serves to contain the blood or body fluids concentrating the effects of the hemostatic agent. Upon dissolving, the release member or film 15, 25, 35 of the present invention will release the amount of hemostatic agent from the delivery assembly directly proximate to the hemorrhage site in a rapid and effective manner. The soluble material may be constructed of any of a variety of thicknesses, thereby controlling the rate at which the release member will dissolve and, as such, the rate at which the hemostatic agent will be delivered to a hemorrhage site, a factor which is also affected by the volume of fluid present. As such, the hemostatic agent delivery system of the present invention may be customized for application to a variety of wounds of varying degrees of severity.

As one example, the hemostatic agent may be applied directly proximate a superficial wound, in which case, the release member or film 15, 25, 35 will preferably include a very thin material so as to permit rapid dissolution and release of the hemostatic agent. For more severe hemorrhages, for example, laceration of a major artery, the release member will include a greater thickness, to assure that the hemostatic agent delivery system 10 may be disposed proximate the hemorrhage site and configured to substantially conform to the wound prior to dissolution of the release member and subsequent release of the hemostatic agent to the hemorrhage site.

In one preferred embodiment, the delivery assembly includes a release member which is disposed in overlying relation to an oppositely disposed support member, the release member being attached to and about a periphery of the support member. More in particular, the release member and the support member are cooperatively structured so as to at least temporarily contain the amount of hemostatic agent for delivery to a hemorrhage site.

In at least one embodiment, the support member includes a sterile dressing, such as, by way of example, an anti-stick gauze pad 1 shown in FIG. 1. It will be appreciated, given the nature of the present invention, that each of the components including the delivery system will be sterilized and packaged utilizing appropriate procedures to assure that a hemorrhage site is not exposed to external contamination. It will be further appreciated, that a support member including a sterile gauze pad will facilitate conforming the hemostatic agent delivery system of the present invention substantially about the configuration of a wound so as to occlude the wound to facilitate the reduction and termination of hemorrhaging therefrom.

This support member may be a flexible support member that may be applied to the healthy tissue surrounding the wound and kept in place using, by way of example only, a flexible adhesive backing which may be sewn, glued, or otherwise mounted to the delivery assembly.

In another embodiment, this support member may be an elastic support member or compression bandage 20 that may be applied to the wound and, by way of example only, be constructed to retain its position without releasing pressure. The delivery assembly may be sewn, glued, or otherwise mounted thereto. The delivery assembly may include a handle member 23a with a base 23b placed on the backside of the elastic support member. The handle serves several purposes, the first of which being to facilitate disposition of the delivery assembly directly proximate to a hemorrhage site, facilitating delivery of the hemostatic agent thereto.

More in particular, the handle 23a is structured and configured to be grasped by one hand of a user and allow the user to quickly and effectively position the delivery assembly including the release member and hemostatic agent with the elastic support member directly onto a hemorrhage site, such as, a lacerated artery. The handle member is attached to the outer face of the support member and disposed opposite the outer surface of the release member 21, and as such, the handle member allows for the user to grasp the delivery assembly with hands that may be wet or bloody, yet avoiding contact with the release member, so as to prevent inadvertent premature release of the hemostatic agent. In addition, the handle 23a may be constructed of a stiff material allowing the medical care giver to exert greater pressure directly on the hemorrhage site. The handle member may be included of a visual indication to facilitate location of the handle member by a user. More in particular, the visual indication may include indicia such as lettering, symbols, stripes, etc., applied directly onto the handle member or may include a color contrast between the support member and the handle which may be a bright color or color pattern.

In another embodiment shown in FIG. 5, this gauze 31, in which a hemostatic composition 34 has been embedded, because of its pliancy, may be rolled into a narrow cylinder-shaped plug 30 allowing for its insertion into a narrow wound opening. This narrow cylinder plug 30 may be inserted into the narrow wound opening using a tampon type applicator with a barrel 33 shown in FIG. 6 and a plunger 36 shown in FIG. 7, allowing for deeper insertion and greater direct pressure on the hemorrhage site. In addition, the cylinder plug 30 may be coated in a soluble release member or PVA film 35 in order to delay release of the hemostatic agent, concentrating the hemostatic agent directly proximate the hemorrhage site.

Formulations

The table below provides information on formulation development.

The first column is a number identifying the formulation. A legend appears after the chart that details the components used in the various formulations.

TABLE 2

| | Gm. Measure by Weight | | | | | | | | | Oz. Measure by Weight | | | | |
|---|---|---|---|---|---|---|---|---|---|---|---|---|---|---|
| | C-25 | C-18 | TEA | H2O | XG | Carag | CG | HEC | Glyc | PPG | EW | Glyc | H2O | LT |
| 1 | 4.5 | | 4.5 | | | | | | | 4 | 2 | | | |
| 2 | 9 | | 9 | 9 | | | | | | 4 | 2 | | | |
| 3 | | 9 | 9 | | | | | | | 5 | 2 | | | |
| 4 | 4.5 | | 4.5 | 9 | | | | | | 4 | 2 | | | |
| 5 | 9 | | 9 | | | | | | | 4 | 2 | | | |
| 6 | | 4.5 | 4.5 | | | | | | | 4 | 2 | | | |
| 7 | | 4.5 | 4.5 | 9 | | | | | | 4 | 2 | | | |
| 8 | 9 | | 9 | | | | | | | 5 | 2 | | | |
| 9 | | | | | 9 | | | | | 4 | 2 | | | |
| 10 | | | | | | 9 | | | | 4 | 2 | | | |
| 11 | | | | | | | 9 | | | 4 | 2 | | | |
| 12 | | | | | | | | 9 | | 4 | 2 | | | |
| 13 | | | | | | | | 9 | | 3 | 2 | 2 | | |
| 14 | | | | | | 9 | | | | 3 | 2 | 1 | | |
| 15 | | | | | | 9 | | | | 3.5 | 2 | 0.5 | | |
| 16 | | | | | | | 18 | | 9 | 4 | 2 | | | |
| 17 | | | | | 9 | | 9 | | | 3 | 2 | 1 | | |
| 18 | | | | | 9 | 9 | | | | 4 | 2 | | | |
| 19 | | | | | 9 | | | | | 4 | 2 | | 0.25 | |
| 20 | | | | | 4.5 | | | | | 4 | 2 | | 0.25 | |
| 21 | | | | | 2.25 | | | | | 4 | 2 | | 0.25 | |
| 22 | | | | | 1.125 | | | | | 4 | 2 | | 0.25 | |
| 23 | | 14.4 | 14.4 | | | | | | | 3 | 2 | | 1 | |
| 24 | | 9 | 9 | | | | | | | 4 | 2 | | 1 | |

TABLE 2-continued

| | Gm. Measure by Weight | | | | | | | | | Oz. Measure by Weight | | | | |
|---|---|---|---|---|---|---|---|---|---|---|---|---|---|---|
| | C-25 | C-18 | TEA | H2O | XG | Carag | CG | HEC | Glyc | PPG | EW | Glyc | H2O | LT |
| 25 | | | 14.4 | 14.4 | | | | | | 2 | 2 | | 2 | |
| 26 | | 14.4 | 14.4 | | | | | | | 5 | 2 | | 0.5 | |
| 27 | | | | | 1.8 | | | | | 3.5 | 2 | | 0.5 | |
| 28 | | | | | 0.9 | | | | | 3.75 | 2 | | 0.25 | |
| 29 | | | | | 1.8 | | | | | 4 | 2 | | 0.5 | |
| 30 | | | | | 2.7 | | | | | 5 | 2 | | 0.5 | |
| 31 | | | | | 2.7 | | | | | 4 | 2 | | 0.5 | |
| 32 | | | | | | 2.7 | | | | 4 | 2 | | 0.5 | |
| 33 | | | | | | | 2.7 | | | 4 | 2 | | 0.5 | |
| 34 | | | | | | | 2.7 | | | 3 | 2 | | 0.5 | |
| 35 | | | | | 2.7 | | | | | 4.5 | 2 | | 0.5 | |
| 36 | | | | | 7.2 | | | | | 4.5 | 2 | | 0.6 | |
| 37 | | | | | 7.2 | | | | | 4 | 2 | | 0.6 | |
| 38 | | | | | | | | | | 4 | | | | 2 |
| 39 | | | | | | | | | | 4 | 1.8 | | | 0.2 |
| 40 | | | | | | | | | | 4 | 1.9 | | | 0.1 |
| 41 | | | | | | | | | | 4.2 | 1.9 | | | 0.1 |
| 42 | | | | | | | | | | 4 | 1.95 | | | 0.05 |
| 43 | | | | | | | | | | 4 | 2 | | | 0.025 |
| 44 | | | | | | | | | | 4.5 | 2 | | | 0.025 |
| 45 | | | | | | | | | | 4.5 | 1.9 | | | 0.1 |
| 46 | | | | | | | | | | 4.2 | 1.9 | | | 0.1 |
| 47 | | | | | | | | | | 4.5 | 1.8 | | | 0.2 |
| 48 | 9 | | 9 | 18 | | | | | | 4 | 2 | | | |

Legend:
C-25 = Carbomer25 (Carbopol ® Aqua SF-1)
C18 = Carbomer18
TEA = Triethanolamine
XG = Xanthan Gum, TIC
Carag = Carrageenan
CG = Cellulose Gum
HEC = Hydroxyethyl Cellulose
Glyc = Glycerin
PPG = Propylene Glycol
EW = Bentone EW (Hectorite Clay)
LT = Bentone LT (Hectorite Clay + Hydroxyethyl Cellulose 50%/50% mixture)
PolySorb = Polysorbate 80

Table 2 represents an evaluation of each formulation number in terms of relative consistency and separation stability.

| | Ideal = 3 Consistency | Ideal = 5 Separation Stability | Notes |
|---|---|---|---|
| 1 | 3 | 3 | |
| 2 | 5 | 4 | |
| 3 | 3 | 2 | |
| 4 | 5 | 4 | |
| 5 | 5 | 5 | |
| 6 | 3 | 3 | |
| 7 | 3 | 3 | |
| 8 | 5+ | 1 | |
| 9 | 4 | 4 | |
| 10 | 3 | 2 | |
| 11 | 3 | 4 | |
| 12 | 3+ | 4 | |
| 13 | 3 | 4 | |
| 14 | too thick | unstable | |
| 15 | too thick | unstable | |
| 16 | too thick | unstable | |
| 17 | too thick | | |
| 18 | too thick | | |
| 19 | too thick | | |
| 20 | too thick | | |
| 21 | 4 | | |
| 22 | 3 | 2-3 | |
| 23 | too thick | | |
| 24 | 3 | 2-3 | |
| 25 | too thick | | |
| 26 | 3 | 3+ | |
| 27 | 5+ | NA | |
| 28 | 5 | NA | |
| 29 | 3 | 4 | Separates after 1 day@room temp, No separation 3 days@150° F. |
| 30 | 3 | 3 | 3 Days@room temp, 3 Days@150° F. |
| 31 | 4 | 4 | 3 Days@room temp, 3 Days@150° F. |
| 32 | 3+ | | Separates after 3 Hrs@room temp. |
| 33 | 3 | 3 | Separates after 3 Days@room temp |
| 34 | 5 | NA | |
| 35 | 3 | 4 | 2 Days@room temp, 3 Days@150° F. |
| 36 | 3− | 3 | 2 Days@150° F., slightly looser than #11 formula |
| 37 | | 3 | 2 Days@150° F. |
| 38 | too thick | 4+ | |
| 39 | 5+ | 5 | |
| 40 | 5 | 5 | Heated |
| 41 | 5 | 5 | Heated |
| 42 | 5 | 3 | Heated |
| 43 | 5 | 3 | |
| 44 | 3 | 2 | |
| 45 | 2 | 2-3 | |
| 46 | 3 | 5 | No absorption |

| | Ideal = 3 Consistency | Ideal = 5 Separation Stability | Notes |
|---|---|---|---|
| 47 | 3 | 3 | Minimal absorption |
| 48 | 3 | 5 | |

Legend Scale:
Consistency = ease of flowability of formula through syringe and product cohesiveness
Consistency Scale = Loose to Stiff (1-5), Ideal = 3
Separation Stability = whether formula in syringe separated after 3 days@room temp and/or 3 days@150° F.
Separation Stability Scale = Failure to None (1-5), Ideal = 5
Formulation 48 - Final Formulation - Tested 3x Freeze/Thaw cycle, and 3 × 150° F., 3 months@–75° F., no separation. Tested absorption rate. Observed excellent absorption with more than eight times liquid volume absorption in <1 minute.

The composition demonstrated stability from 32° F.-150° F.

A composition based on formulation 48 was tested as set forth below.

The composition was tested and found to exhibit the following characteristics:

Adhesion Strength

A small amount of a composition of formula 48 was tested for a determination of the adhesive strength of the product at four coating thicknesses. A small spring type tensiometer (Hunter Spring brand) was connected to small wooden blocks having two smooth surfaces (each 2.25 sq.in) to be coated with the composition. The test would determine the pull strength (psi) required to cause the composition to fail.

Summary of Adhesion Test Data for Medical Paste

| Coating Test No. | Adhesion Thickness | (psi) |
|---|---|---|
| 1 | <15 mil (0.015 in.) | 1.078 |
| 2 | 1/32 in. (0.0312 in.) | 0.542 |
| 3 | 1/16 in. (0.0625 in) | 0.258 |
| 4 | 1/8 in. (0.125 in.) | 0.230 |

(1) The hemostatic composition shows good adhesion (greater than 1 pound per square inch) for very thin coatings between two wooden test surfaces.

(2) For a coating thickness of 1/32 inch the adhesion drops to 0.542 psi.

(3) For a coating of 1/16 inch or greater, the adhesion drops further.

Viscosity

A composition according to formula 48 tested kinematic viscosity at room temperature (25° C.) using a Brookfield Viscometer, Model No. RVF.

Results
Kinematic Viscosity: 356,000 cps
(Spindle 7, at 4 RPM)
cps=Centipoises

EXAMPLES

In one embodiment, the formulation includes:

| | |
|---|---|
| Propylene Glycol (PPG) | 55.56% |
| Hectorite | 27.78% |
| H2O | 8.34% |
| Carbomer (Carbopol ® Aqua SF-1)) | 4.17% |
| Triethanolamine (TEA) | 4.17% |

The composition is prepared by:
1. Mixing Carbomer and H2O
2. Add in TEA and mix
3. Add PPG and mix
4. Add hectorite and mix The resulting mixture has a viscosity of more than 50,000 CPs.

The pH of the composition is 7.68 and the specific gravity is 1.2773. This specific gravity has the added benefit of preventing dispersion of the mixture even against major arterial bleeding.

A preferred hectorite has a particle size of 95% less than 0.076 mm (less than 76 μm, or 76 microns).

An advantage of the present invention is the composition does not interfere with the chemical-physiological processes of the coagulation process. That is to say, the chemical, physical, and physiological processes of both intrinsic and extrinsic blood coagulation mechanism are not affected by the hemostatic composition of the present invention.

One mechanism that has been observed is the composition absorbs more than eight times its weight of water in less than one minute. Thus, the concentration of blood platelets and coagulation proteins are increased and results in the composition having an increased ability to accelerate and maintain blood clots.

The propylene glycol in the composition is a humectant and helps impart upon the composition a hydrophilic matrix that provides increased and accelerated absorption through the various layers. The addition of a dispersal agent in the clay accelerates yet further the absorption process and capacity.

The formulation of the composition itself presented a problem in providing a suitable liquid carrier to deliver the clay to a wound that would not itself cause the clay to swell thereby negating its hemostatic properties of absorption prior to application.

The composition formulation of the present invention has successfully addressed and solved this difficulty by preparing a stable viscous liquid carrier composition that will deliver the clay to a wound site without causing the clay to reduce its water absorption capacity. The percentage of water in the formulation used to promote the dispersal of the suspension agent is offset many times over by the benefits of the addition of the humectant, propylene glycol. Thus an optimal water percentage of less than about 10% is relatively small, yet does not affect the stability of the composition during the manufacturing process. After embedding in the composition in the gauze, it is then dehydrated removing even that relatively small percentage of water, optimizing yet further, the hemostatic agent.

The composition, once rehydrated by contact with blood, has an increased elasticity that allows it to conform even more to a particular shape at a wound site. In addition, due to this elasticity factor, the clot remains stable and will not rupture.

The composition of the present invention not only provides rapid and critical assistance in the blood clotting process, but allows for the administration of fluids, which may also be critical to the survival of a patient while not interrupting or disturbing the therapeutic effect of the administered composition. Under many conventional medical protocols and procedures, patients with traumatic wounds do not receive fluids until they reach the operating theatre for fear that the accompanying elevated blood pressure will cause rebleeding.

The present composition has demonstrated the proper adhesive strength such that it remains in contact with tissue at and/or near a wound site in spite of a buildup of hydrostatic pressure from bleeding. This adhesion affords the composition sufficient contact time to promote clotting, even in cases of major arterial bleeding. This adhesive property provides an additional benefit in that using the composition of the present invention does not require pressure to be applied in order to facilitate a blood clot.

Although the composition has an elevated viscosity, it has been observed that the viscosity and adhesion qualities of the composition, once rehydrated by contact with blood, do not hinder subsequent removal after a blood clot has formed. The composition may be removed as desired by conventional wound irrigation techniques. These wound irrigation techniques are sufficient to remove the composition once it is observed that blood flow has substantially decreased and or/stopped.

In one embodiment shown in FIGS. 5-7, the composition of the present invention is contained within an ejection delivery system such as, by way of example only, a tampon type applicator barrel 33 and plunger 36. This applicator may deliver the present invention through a narrow opening directly to a hemorrhage site.

The ejection delivery system offers many advantages. The system may deliver the hemostatic agent through a narrow opening. Even if one cannot see the actual hemorrhage site, the hemostatic agent may be introduced through an entry point in the skin from an object, such as a bullet, shrapnel and the like, close to the hemorrhage site insert the ejection device. Thus, treatment may occur even if the hemorrhage site cannot be seen. There is no need to evacuate blood from a wound and, in using a flexible ejection device, there is no need to enlarge a wound site causing additional trauma in order to administer the hemostatic agent.

In using an ejection device to deliver the hemostatic agent, a patient may be able to self-administer using one hand. Many current protocols and procedures require wound enlargement, blood evacuation, and application by more than one medical care giver in some cases which is not required using this delivery system. A further advantage of the ejection delivery system is that it does not require any special training to administer. Most other wound treatments currently in use require extensive medical training to administer and may not be self-administrable.

While the invention has been described in its preferred forms or embodiments with some degree of particularity, it is understood that these descriptions have been given only by way of example and that numerous changes in the details of construction, fabrication, and use, including the combination and configuration of parts, may be made without departing from the spirit and scope of the invention.

The invention claimed is:

1. A system for delivering a hemostatic agent to a wound, the system comprising:
   a composition of a hemostatic hectorite clay material combined with a glycol humectant in a stable suspension, said glycol humectant in said stable suspension acting to create a hydrophilic matrix and said composition including:
   a) 40-70% propylene glycol;
   b) 20-40% hectorite clay;
   c) 5-15% $H_2O$;
   d) 1-10% carbomer; and
   e) 1-10% triethanolamine; and
   an absorbent mesh fabric having said composition embedded therein to adhere to the wound, permit at least some of said composition to come into contact with a bleeding source, effect hemostasis of bleeding, accelerate stable clotting, prevent displacement of said composition by arterial pressure and be easily removed;
   said stable suspension allowing for increased embedment in said mesh fabric matrix and acting to create elasticity providing wound conformation.

2. The system according to claim 1, wherein said hemostatic hectorite clay material includes a hectorite clay in which 95% of the hectorite in said hectorite clay has a particle size of less than 76 microns.

3. The system according to claim 2, wherein said hectorite clay is beneficiated with an addition of a dispersal agent and by a reduction of its ferric and ferrous oxide content, and said composition absorbs a weight of liquid greater than a weight of said composition.

4. The system according to claim 1, wherein said composition absorbs a weight of liquid more than twenty four times a weight of said composition and said composition absorbs a weight of liquid more than eight times greater than a weight of said composition in approximately one minute or less.

5. The system according to claim 1, wherein said composition is inert relative to blood clotting proteins, blood platelets, extrinsic blood clotting mechanisms and intrinsic blood clotting mechanisms, and said absorbent mesh fabric is configured to apply said composition directly to an external wound.

6. The system according to claim 1, wherein:
   a) said propylene glycol percentage is 55.56%;
   b) said hectorite clay percentage is 27.78%;
   c) said $H_2O$ percentage is 8.34%;
   d) said carbomer percentage is 4.17%;
   e) said triethanolamine percentage is 4.17%; and
   said composition exhibits a kinematic viscosity of more than 100,000 cps.

7. A method of accelerating blood clotting of a wound, the method comprising the following steps:
   locating a wound;
   providing a composition of a hemostatic hectorite clay material combined with a glycol humectant in a stable suspension, the glycol humectant in the stable suspension acting to create a hydrophilic matrix and the composition including 40-70% propylene glycol, 20-40% hectorite clay, 5-15% $H_2O$, 1-10% carbomer and 1-10% triethanolamine;
   providing an absorbent mesh fabric having the composition embedded therein to adhere to the wound, permit at least some of the composition to come into contact with a bleeding source, effect hemostasis of bleeding, accelerate stable clotting, prevent displacement of the composition by arterial pressure and be easily removed;
   the stable suspension allowing for increased embedment in the mesh fabric matrix and acting to create elasticity providing wound conformation; and
   applying the absorbent mesh fabric having the composition into the wound.

8. The method according to claim 7, wherein the wound is an internal wound not being readily visible or locatable from outside a patient, the step of applying the composition is carried out from a support member, and an application site of the hemostatic agent composition is irrigated to remove substantially all of the hemostatic agent composition.

9. The system according to claim 1, which further comprises a release member with a soluble material fabricated from a hydrophilic material for dissolving and releasing an amount of said hemostatic material upon disposition proximate to the wound, said release member dissolves at the wound, said release member includes a film formed or placed over said hemostatic material, and said release member is polyvinyl alcohol.

10. The system according to claim 1, which further comprises other materials to be added to said hemostatic material to provide ancillary benefits to clotting or fluid absorbing functions of said hemostatic material, said other materials including antiseptics.

11. The system according to claim 1, which further comprises:
- a flexible support member;
- said mesh fabric being mounted on said flexible support member;
- said glycol humectant being propylene glycol; and
- said hectorite clay material being combined with said propylene glycol in said stable suspension in a dehydrated form.

12. The system according to claim 11, which further comprises a soluble film formed or placed over said clay-embedded mesh fabric, said flexible support member being a flexible adhesive support member for adhering to the skin of a patient.

13. The system according to claim 11, which further comprises a handle or other stiff retentive member attached to said flexible support member on a side opposite said clay-embedded mesh fabric, said flexible support member being a flexible elastic support member configured to exert and retain pressure on a wound site.

\* \* \* \* \*